United States Patent
Lee et al.

(10) Patent No.: US 9,958,088 B2
(45) Date of Patent: May 1, 2018

(54) MICROVALVE USING SURFACE TENSION, MICROFLUIDIC CHIP COMPRISING SAME, AND METHOD FOR MANUFACTURING SAME

(75) Inventors: Sang Hoon Lee, Gyeonggi-do (KR); Edward Kang, Gyeonggi-do (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 1228 days.

(21) Appl. No.: 13/988,892

(22) PCT Filed: Nov. 23, 2011

(86) PCT No.: PCT/KR2011/008954
§ 371 (c)(1),
(2), (4) Date: Dec. 12, 2013

(87) PCT Pub. No.: WO2012/070860
PCT Pub. Date: May 31, 2012

(65) Prior Publication Data
US 2014/0175711 A1   Jun. 26, 2014

(30) Foreign Application Priority Data
Nov. 24, 2010 (KR) ........................ 10-2010-0117572

(51) Int. Cl.
*F16K 99/00* (2006.01)
*D01D 5/00* (2006.01)
(Continued)

(52) U.S. Cl.
CPC ............ *F16K 99/0015* (2013.01); *D01D 5/00* (2013.01); *D01F 6/84* (2013.01); *D01F 9/00* (2013.01); *D01F 9/04* (2013.01); *F16K 99/0017* (2013.01); *F16K 99/0055* (2013.01); *F16K 99/0059* (2013.01); *G01N 2035/00158* (2013.01); *Y10T 29/49412* (2015.01); *Y10T 156/1002* (2015.01)

(58) Field of Classification Search
CPC ............ F16K 99/0015; F16K 99/0017; F16K 99/0055; F16K 99/0059; D01D 5/00; D01F 6/84; D01F 9/00; D01F 9/04; F04B 19/006; G01N 2035/1034; B01L 3/5027; F15C 5/00
See application file for complete search history.

(56) References Cited

PUBLICATIONS

"A pneumatically controllable flexible and polymeric microfluidic valve fabricated via in situ development"; Ju Yeaul Baek et al; J. Micromech. MicroEng. 15 (2005) 1015-1020.*

* cited by examiner

*Primary Examiner* — Joseph S Del Sole
*Assistant Examiner* — John Robitaille
(74) *Attorney, Agent, or Firm* — Womble Bond Dickinson (US) LLP

(57) ABSTRACT

The present disclosure relates to a microvalve using surface tension, a microfluidic chip including same and a method for manufacturing same. More particularly, the present disclosure relates to a microvalve using surface tension, a microfluidic chip including same and a method for manufacturing same, wherein the microvalve can be manufactured through a simple process and the microvalve and a coaxial sample channel are not separated, and thus the microvalve may be easily installed not only in an existing quadrangular channel but also in the coaxial channel so as to control the flow and amount of a microfluid (sample).

4 Claims, 15 Drawing Sheets

(51) Int. Cl.
*D01F 6/84* (2006.01)
*D01F 9/00* (2006.01)
*D01F 9/04* (2006.01)
G01N 35/00 (2006.01)

[Fig. 1]
a
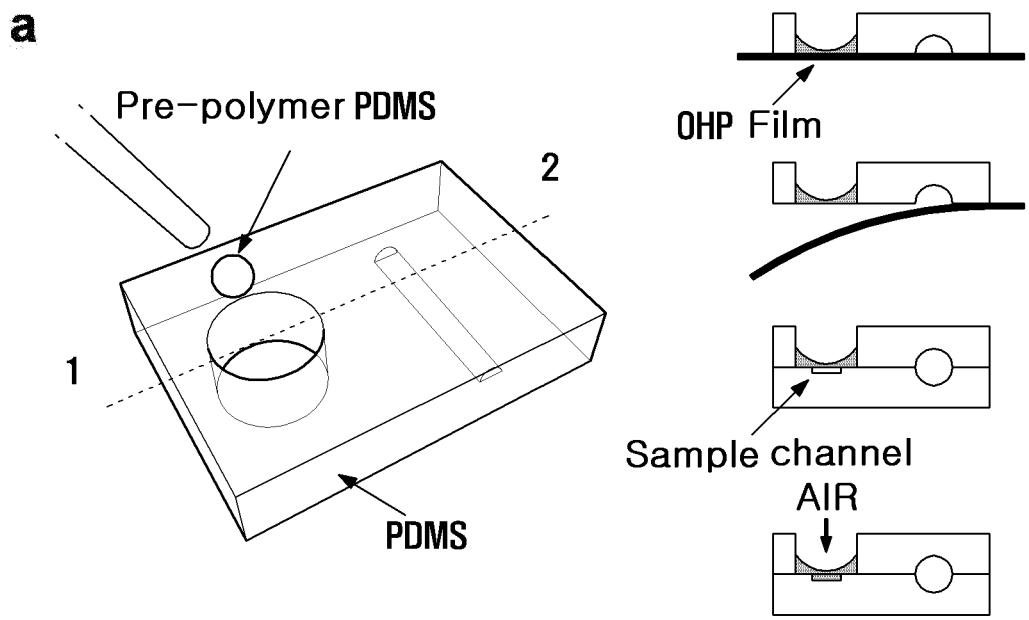
b
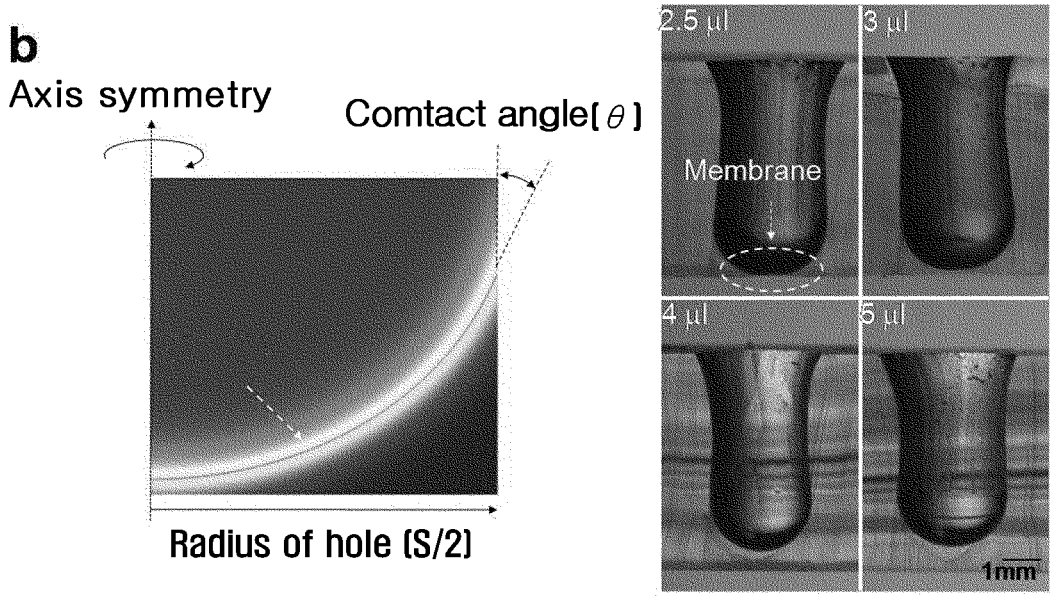

[Fig. 2]
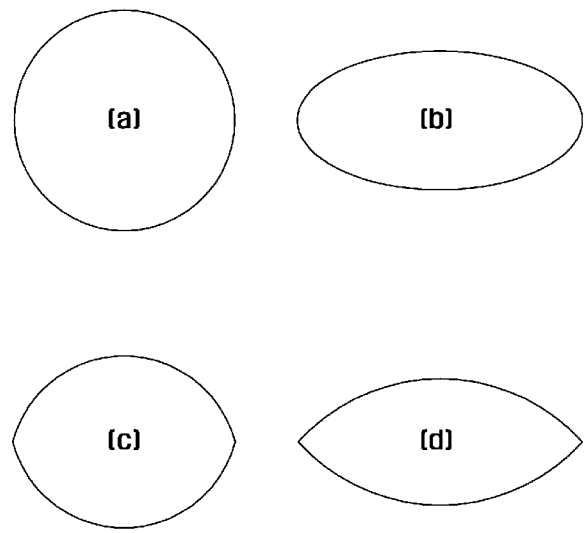

[Fig. 3]
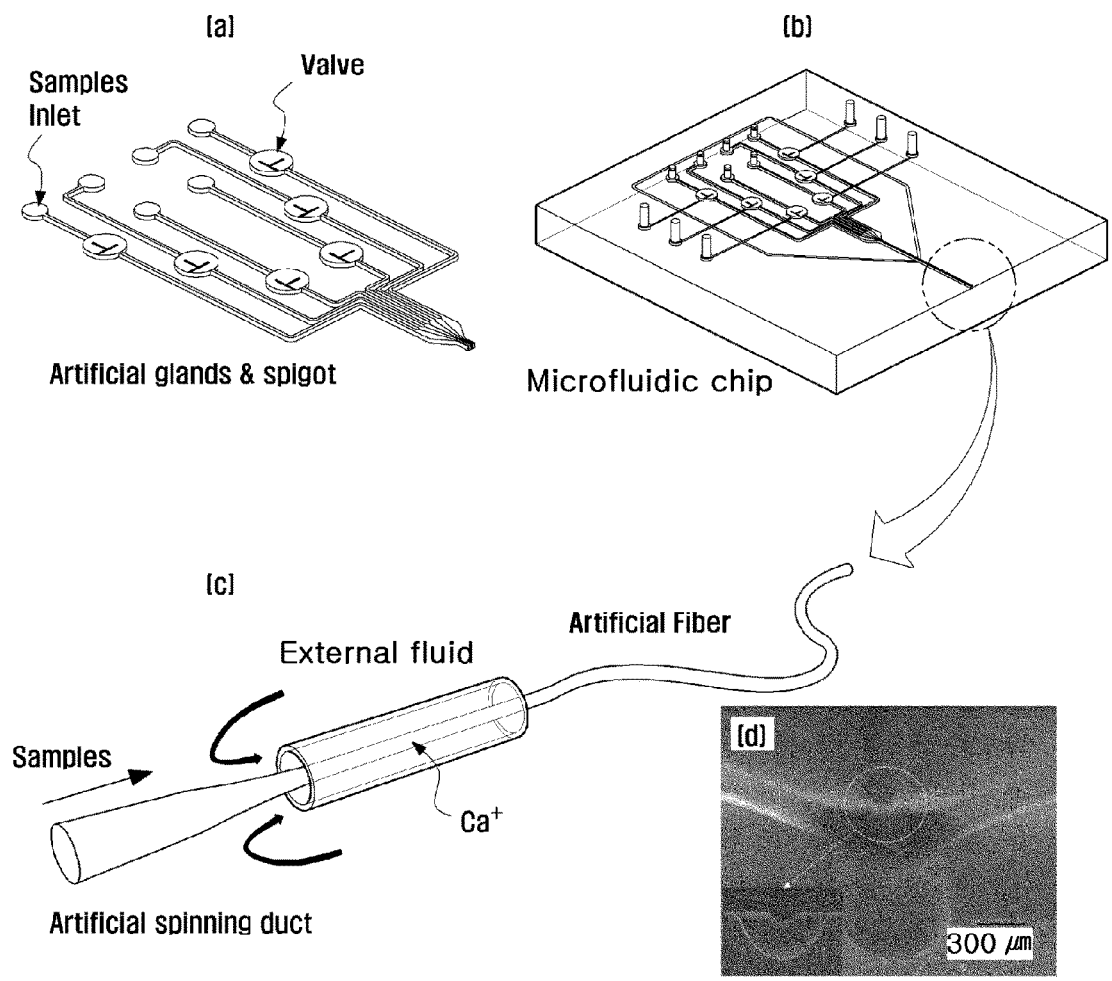

[Fig. 4]
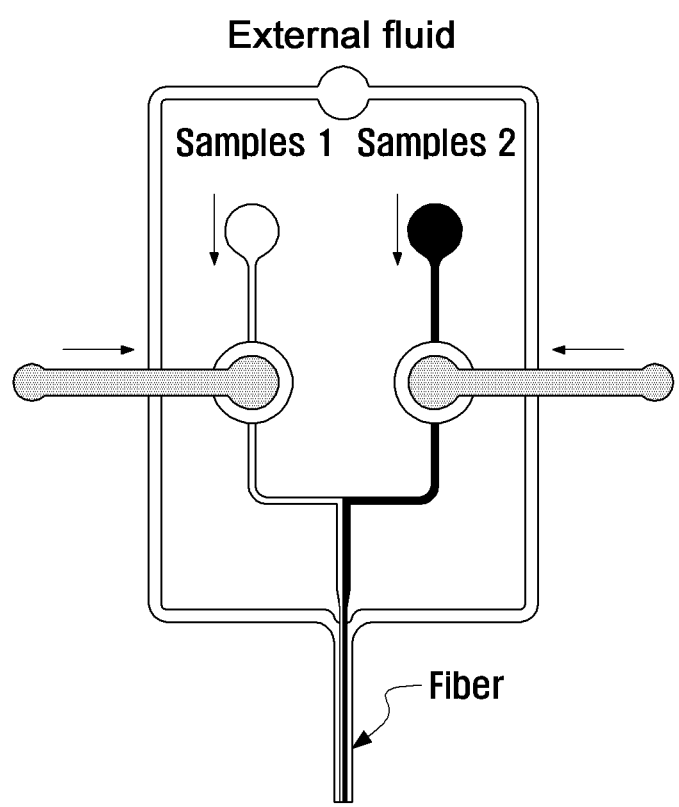

[Fig. 5]
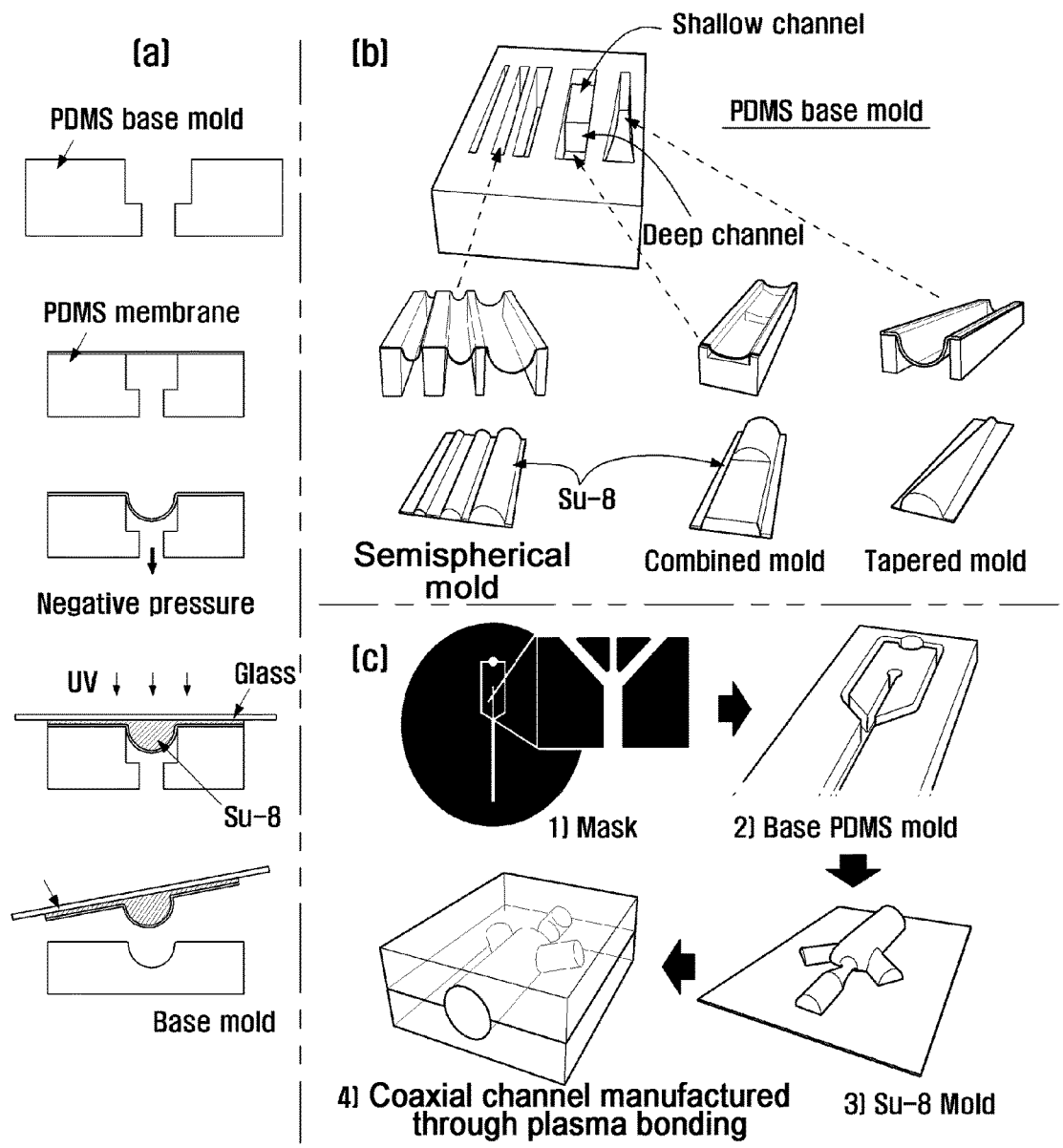

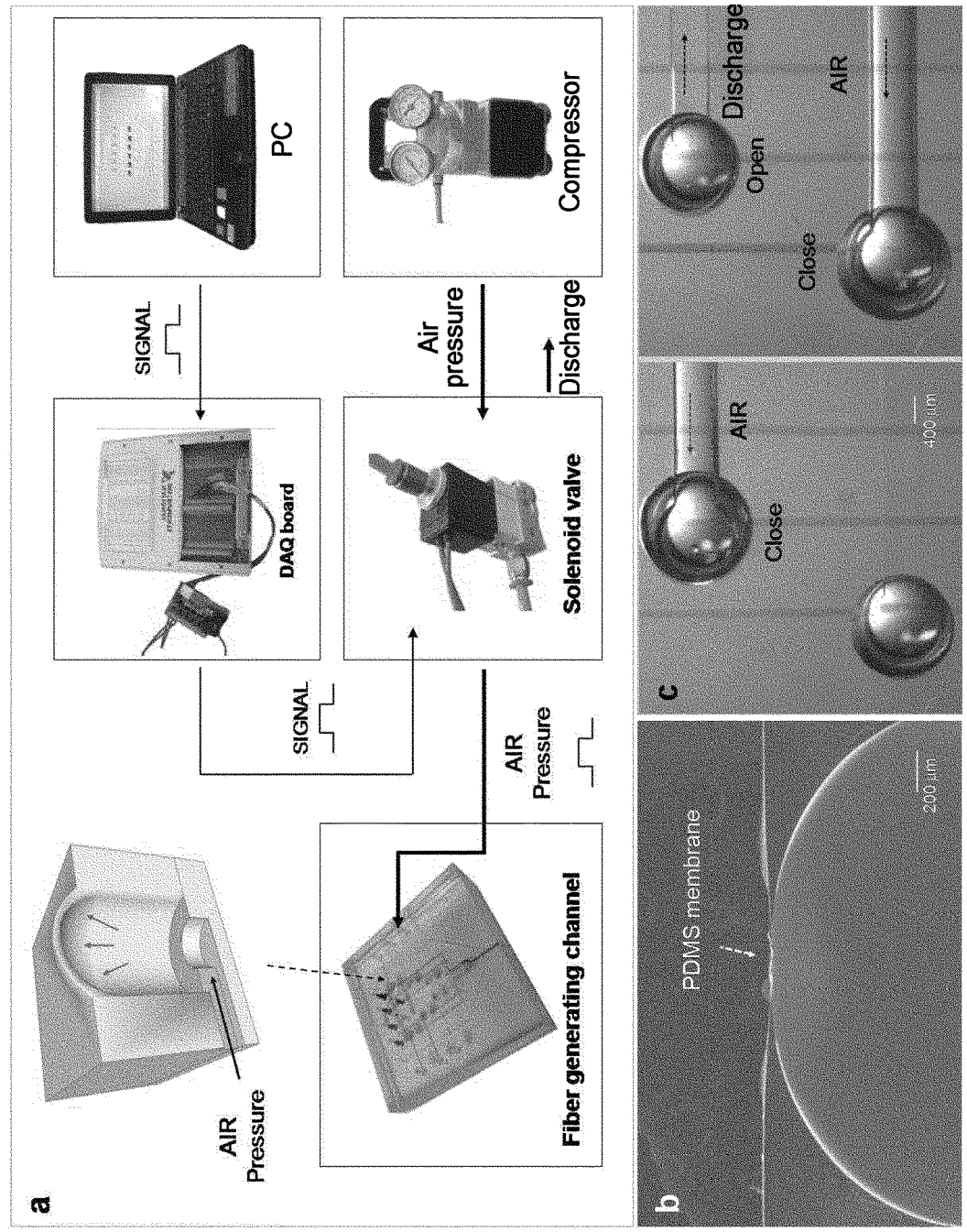
[FIG. 6]

[Fig. 7]
[Fig. 8]
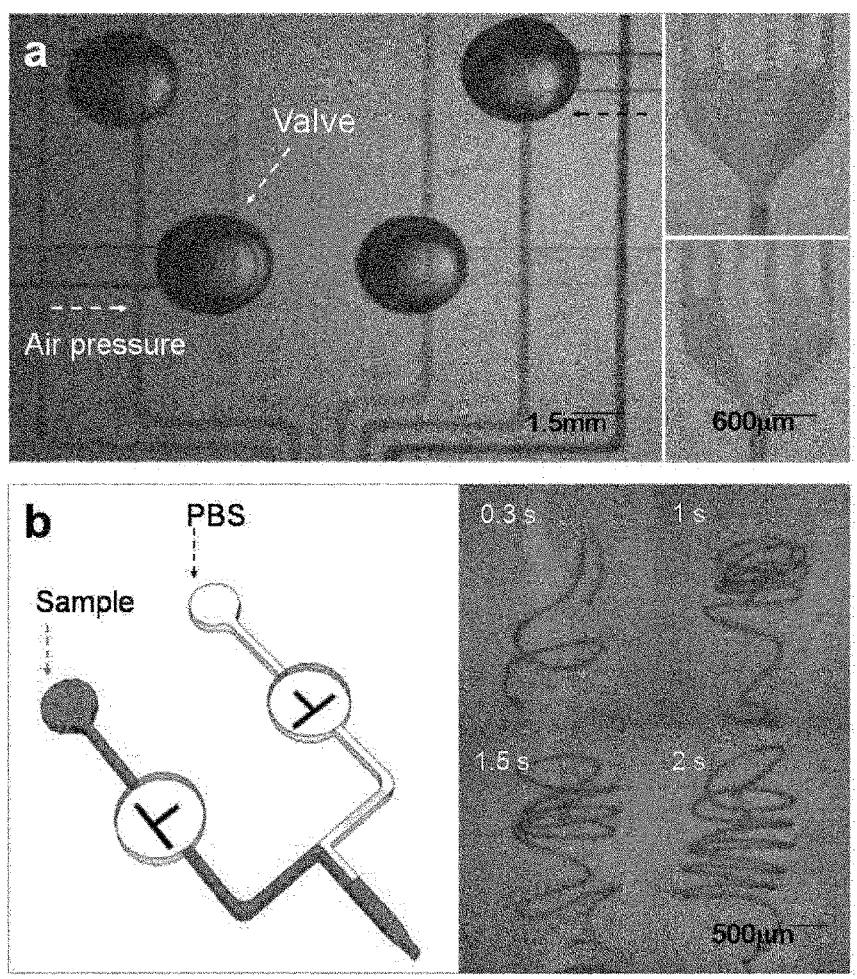

[Fig. 9]
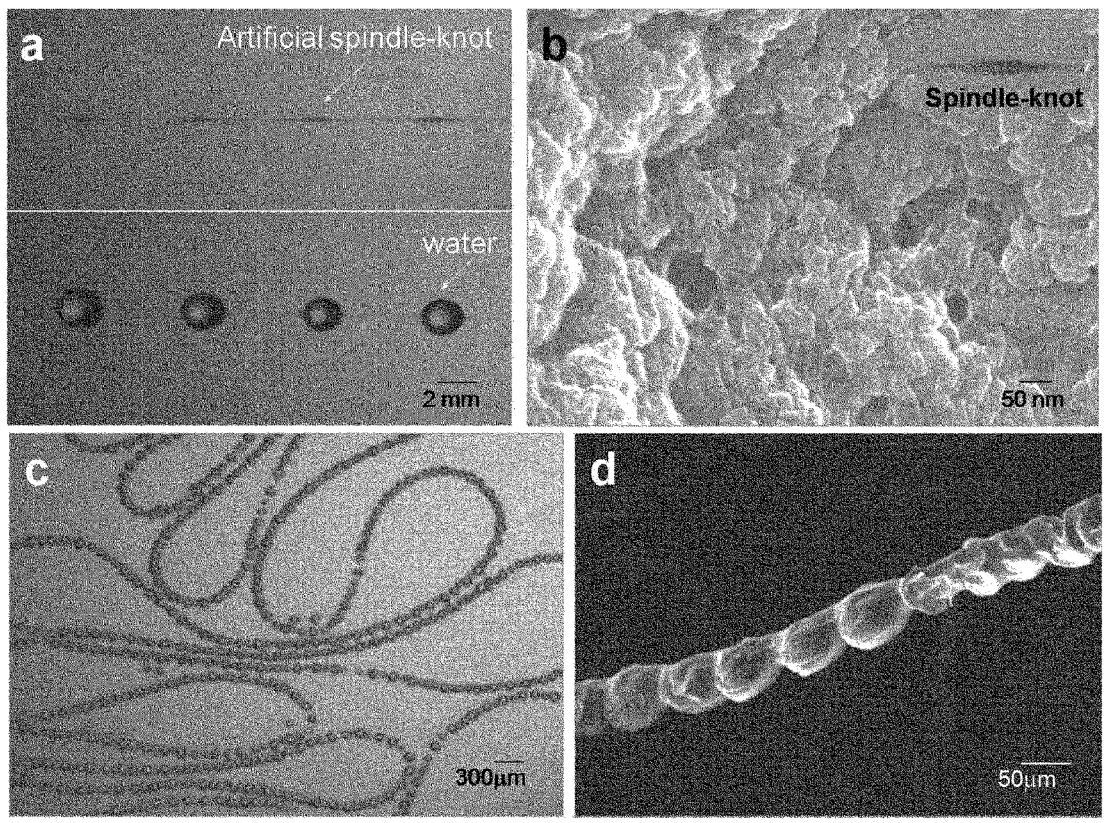
[Fig. 10]
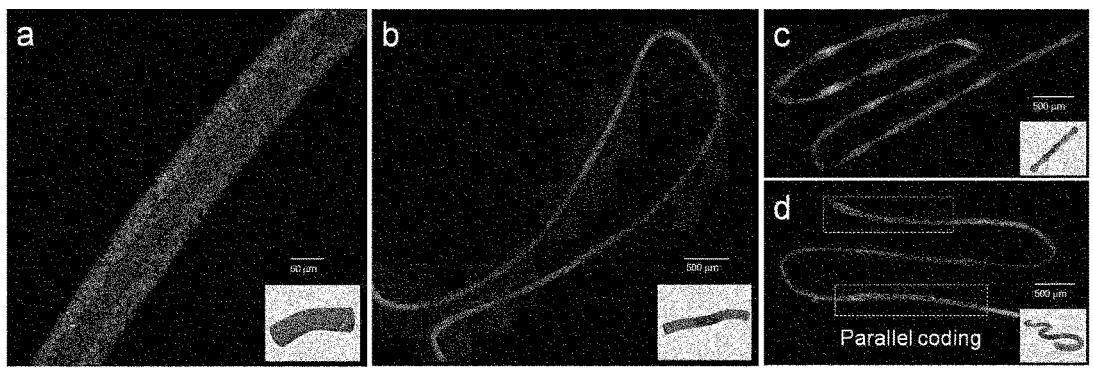

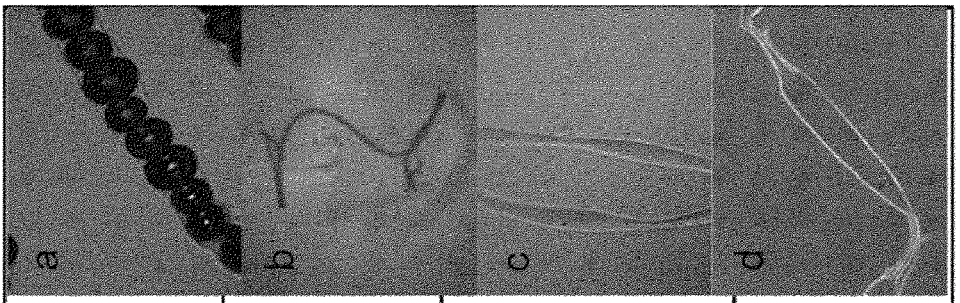
[Fig. 11]

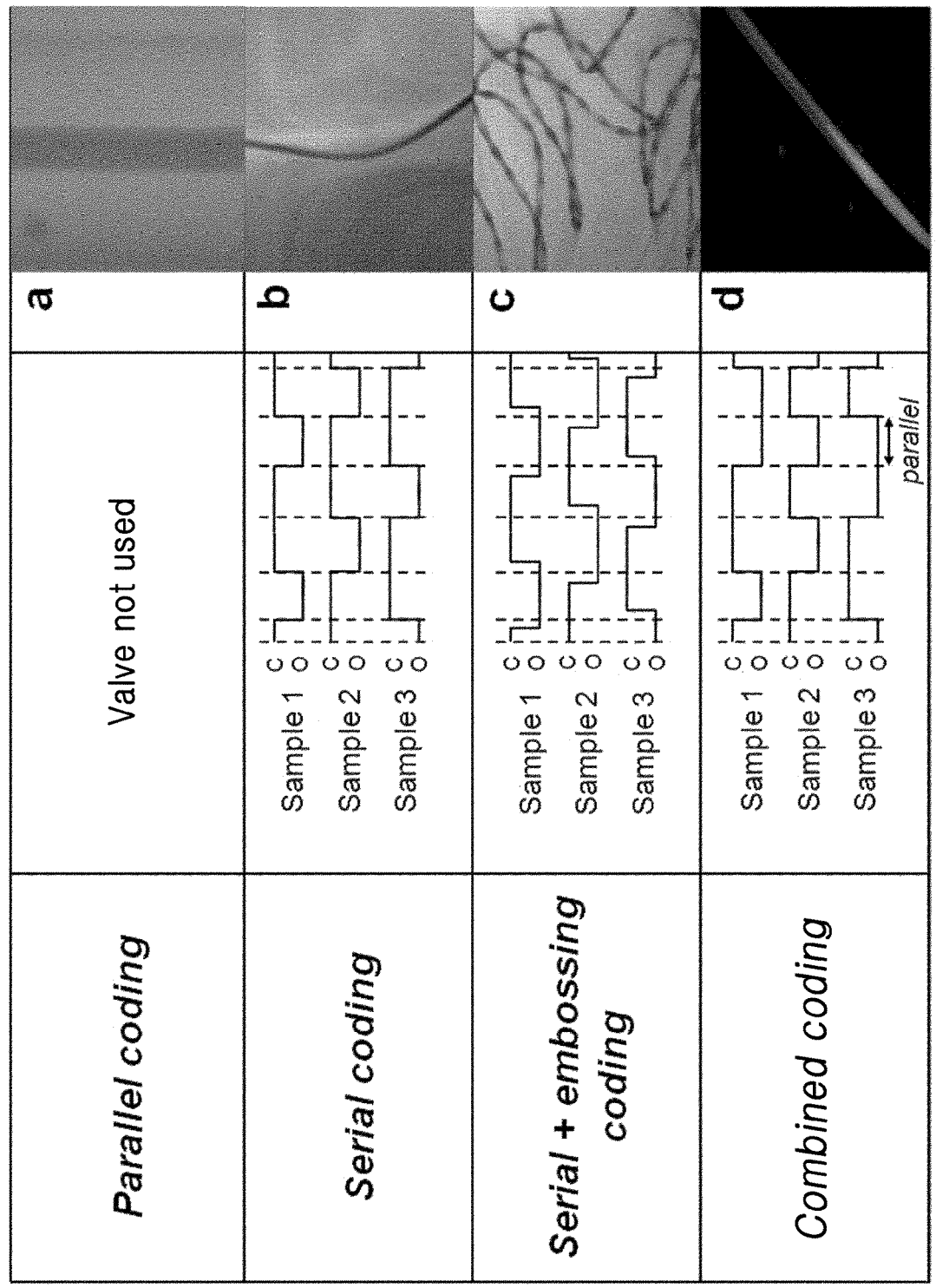
[Fig. 12]

[Fig. 13]
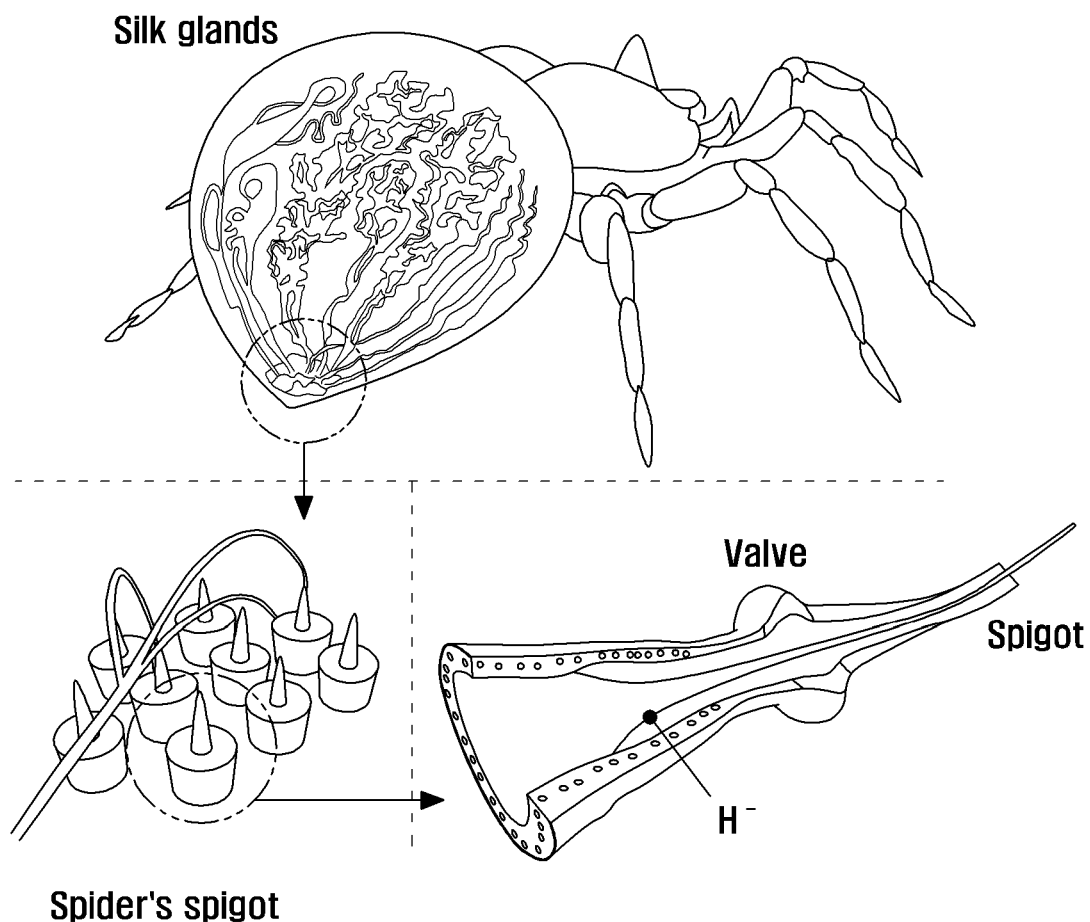

[FIG. 14]
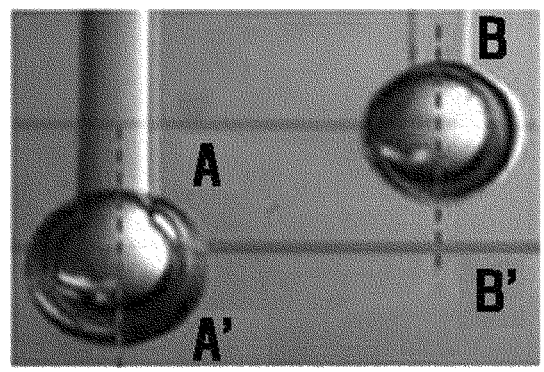
Parabolic membrane
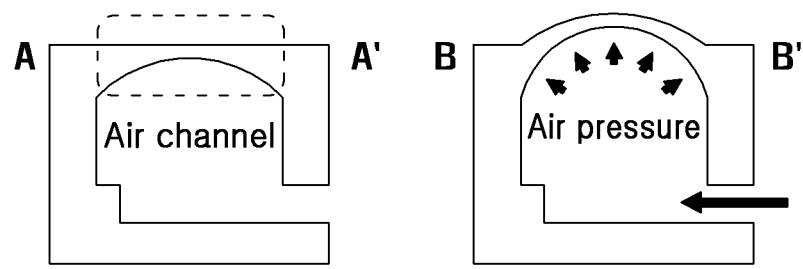
[Fig. 15]
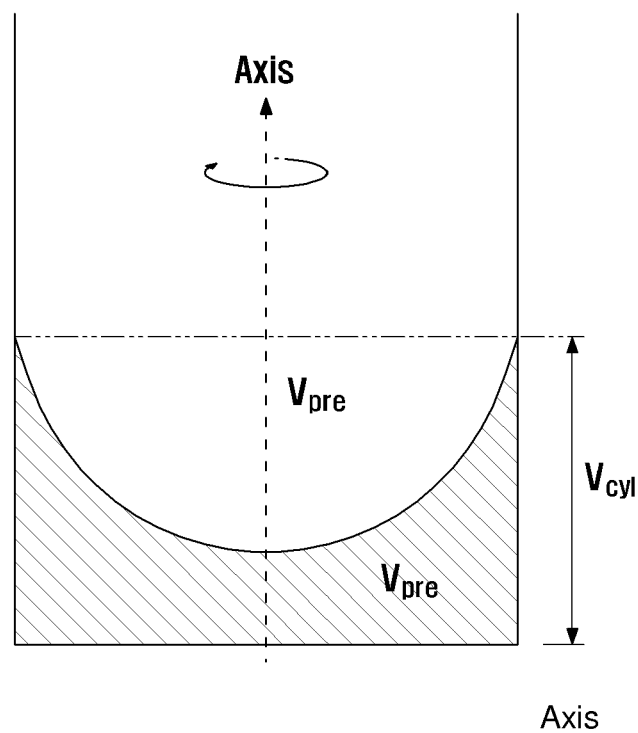

[Fig. 16]
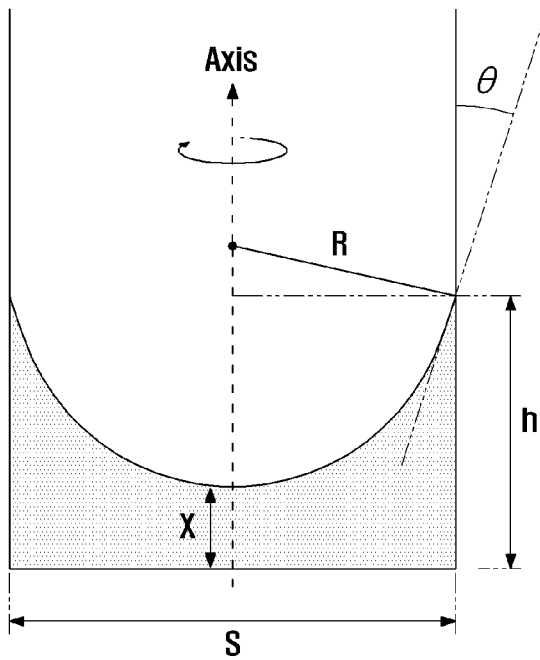
[Fig. 17]
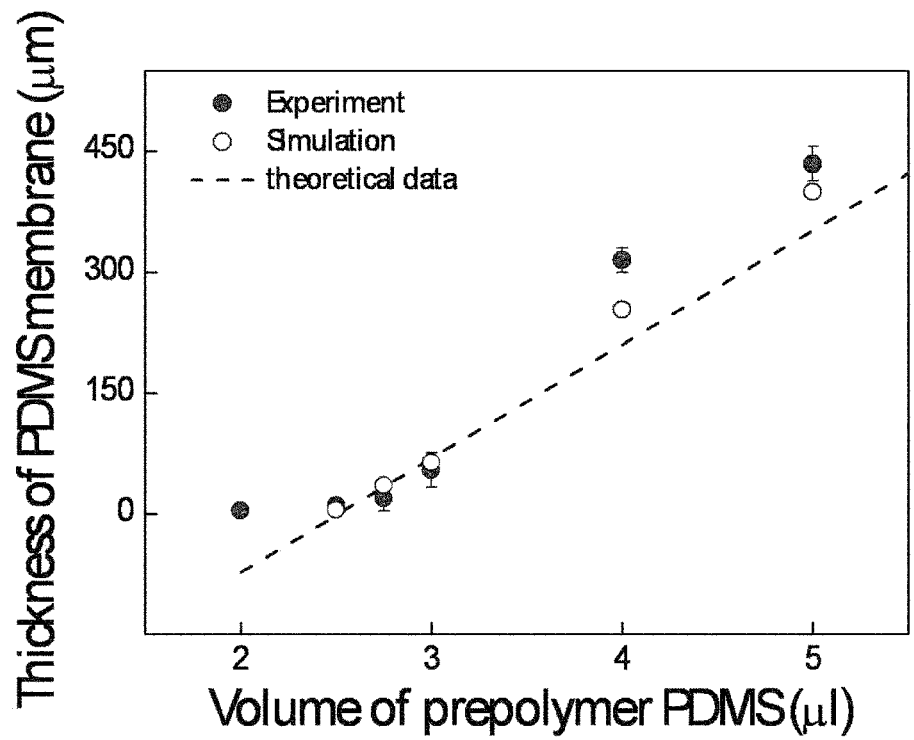

[Fig. 18]
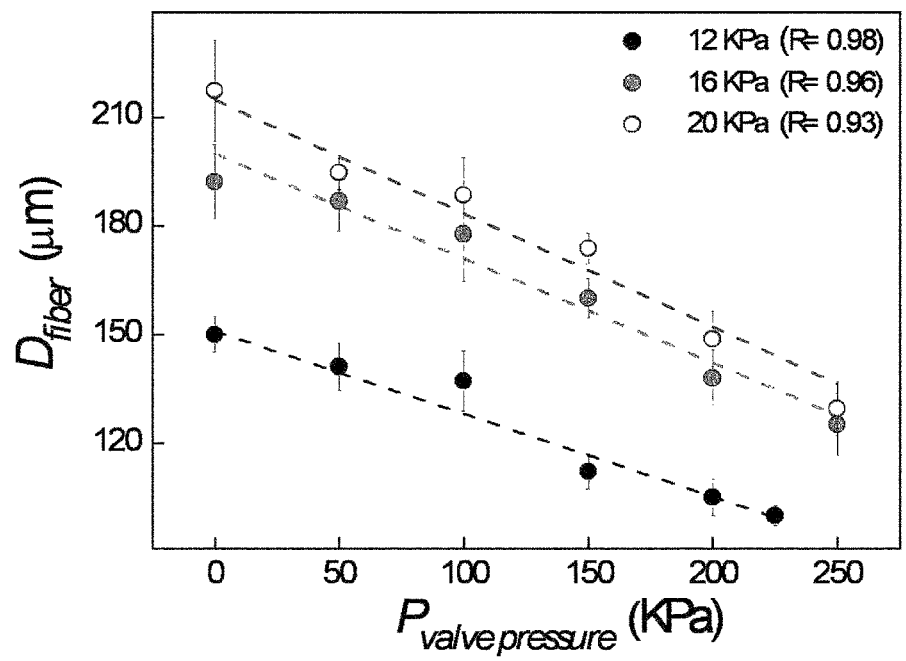
[Fig. 19]
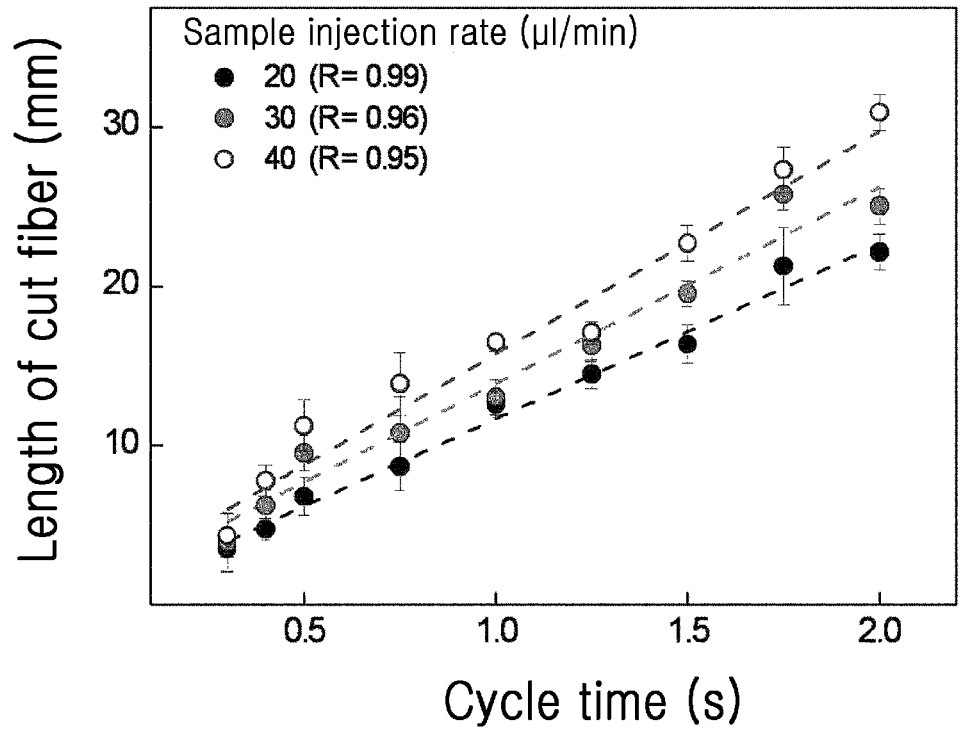

[Fig. 20]
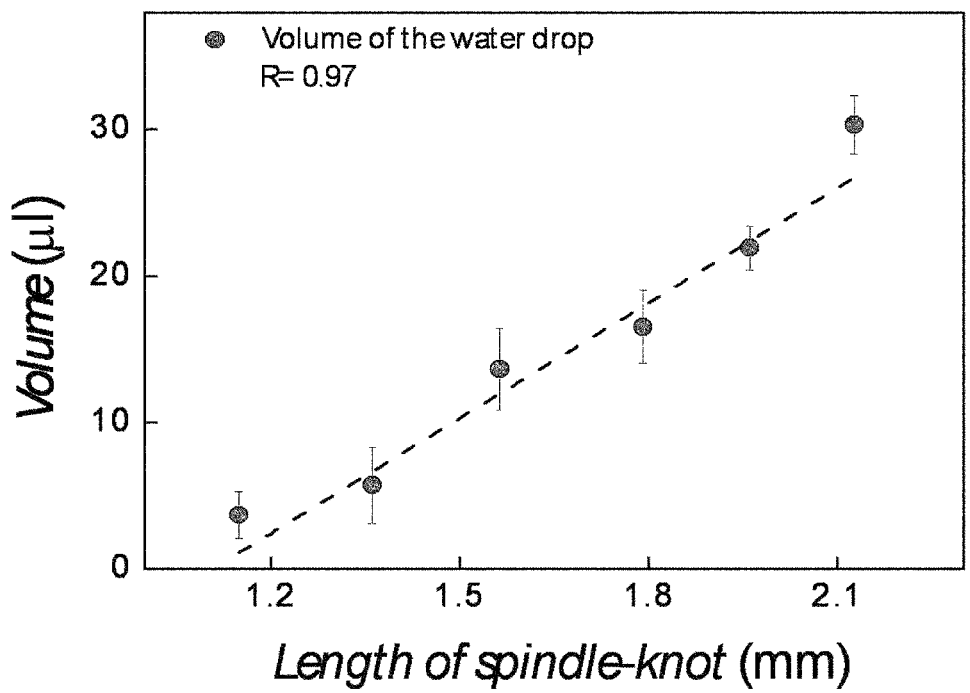

MICROVALVE USING SURFACE TENSION, MICROFLUIDIC CHIP COMPRISING SAME, AND METHOD FOR MANUFACTURING SAME

TECHNICAL FIELD

The present disclosure relates to a microvalve using surface tension, a microfluidic chip including same and a method for manufacturing same. More particularly, the present disclosure relates to a microvalve using surface tension, a microfluidic chip including same and a method for manufacturing same, wherein the microvalve can be manufactured through a simple process and the microvalve and a coaxial sample channel are not separated, and thus the microvalve may be easily installed not only in an existing quadrangular channel but also in the coaxial channel so as to control the flow and amount of a microfluid (sample).

BACKGROUND ART

Microfluidic chips including microchannels contribute a lot to developments in the fields of cell biology, chemical engineering and medical engineering by enabling small-scale experiments. Many parts of microfluidic chips are being developed, including mixers, valves and sorters. Among them, the valve is studied a lot since it allows free flow of a fluid in the chip and control of the sample amount.

A few schemes have been presented thus far. The most commonly employed method is to attach a thin elastic polymer membrane between two chips and blocking the channel of the upper or lower chip using external pressure. However, to insert the membrane, the upper and lower chips have to be separated completely and this process is complicated in control of the thin membrane.

There is another method that uses a hydrogel. In this method, fluid flow is controlled by controlling the motion of the material which is sensitive to electric field or pH in the channel. However, this method is very difficult to realize and is inapplicable to long-term use for a sensitive sample since it can be affected by the electric field or pH.

DISCLOSURE

Technical Problem

The present disclosure is directed to providing a microvalve capable of overcoming the above-described and other problems, a method for manufacturing same, a microfluidic chip including same, a method for manufacturing same and a method for manufacturing microfibers or microparticles of various shaped using same.

Technical Solution

In an aspect, the present disclosure provides a microvalve including a thin membrane made of a polymer below a hole 1.5-4 mm in diameter which perforates a microfluidic chip.

In another aspect, the present disclosure provides a method for manufacturing a microvalve, including: (a) making a hole perforating a microfluidic chip; (b) placing the chip on a film; (c) forming a thin membrane by injecting a liquid polymer into the hole; (d) curing the thin membrane; and (e) removing the film.

In another aspect, the present disclosure provides a method for bonding the microvalve with a coaxial sample channel.

In an exemplary embodiment, the channel desired to be controlled by the microvalve is positioned below the valve. In other words, the microvalve is positioned on the coaxial sample channel desired to be controlled such that the membrane of the microvalve is bonded with the coaxial channel through oxygen plasma bonding and remains not completely separated.

In another aspect, the present disclosure provides a microfluidic chip including a first layer including an air channel, a second layer including a microvalve and a third layer including a coaxial sample channel.

In an exemplary embodiment, the microfluidic chip may control a fluid with its upper and lower portions not being completely separated.

In another aspect, the present disclosure provides a method for manufacturing the microfluidic chip.

In an exemplary embodiment, the present disclosure provides a method for manufacturing a microfluidic chip, including: positioning a coaxial sample channel below a membrane of a microvalve and bonding them through oxygen plasma bonding; and positioning an air channel on the microvalve to which the sample channel is bonded and bonding them through oxygen plasma bonding.

In another aspect, the present disclosure provides a coaxial channel and a method for manufacturing same.

In another aspect, the present disclosure provides a method for manufacturing a microfiber using the microfluidic chip.

In an exemplary embodiment, the present disclosure provides a method for manufacturing microfibers of various shapes, lengths and sample amounts using the microfluidic chip.

In another aspect, the present disclosure provides a method for manufacturing a microparticle using the microfluidic chip.

Accordingly, the present disclosure may be widely applied for synthesis of fibers and particles for use in the fields of biomedicine, tissue engineering and drug delivery.

Hereinafter, the terms used in the present disclosure are described.

The term 'prepolymer' refers to a polymer before curing.

The term 'prepolymer PDMS' refers to PDMS before curing. In order to manufacture a PDMS chip, a PDMS base is mixed with a curing agent at 10:1. The resulting mixture is poured into a cast master mold and cured in an oven at 80° C. for about 1 hour. The mixture is defined as the prepolymer PDMS and is used to manufacture a valve according to the present disclosure (see FIG. 1). Since the prepolymer PDMS has the same surface property as the PDMS chip, the contact angle is very large. Therefore, it is possible to manufacture a thin membrane (valve) in the middle of a hole of the PDMS chip.

Advantageous Effects

A microfluidic chip according to the present disclosure, in which the upper and lower portions are not completely separated, allows formation of a channel bonded with the valve, thus improving the function of the valve and reducing size.

And, since a semipermanent material is used, operation life is greatly improved.

Further, since the intrinsic property of the material, i.e. surface tension, is used, the manufacturing process is very easy and highly reproducible.

Since the valve is bonded with the coaxial channel, a desired effect can be achieved with channels of various shapes, not just the existing quadrangular channel.

In particular, the coaxial channel allows manufacturing of microfibers, not only in cylinder shape but various shapes.

When two semicylindrical channels are bonded as a cylinder channel, a microfiber can be manufactured by operating the valve. For this, a valve portion and a microfiber generating portion are prepared.

Microfibers of various shapes and different sample amounts can be prepared using same.

Also, coded fibers can be manufactured very easily by controlling fluid flow and sample amount.

DESCRIPTION OF DRAWINGS

FIG. 1a schematically shows a procedure of manufacturing a chip wherein a microvalve is bonded with a coaxial channel. An upper portion (or a lower portion) of a chip having a small hole (2-3 mm or larger in diameter) is attached on an OHP film and a calculated amount of PDMS is dropped thereon. After thermal curing, the film is bonded to the channel therebelow. The channel may be blocked by injecting air from the upper portion of the valve.

FIG. 1b shows a result of 2D simulation along the cross section of a microvalve according to the present disclosure. The images on the right side show a cross section of an actually manufactured valve.

FIG. 2 shows cylinder channels of various shapes obtained by bonding two molded parts of semicylindrical channels.

FIG. 3[a] schematically shows a microfluidic chip having six sample channels, FIG. 3[b] shows an actually manufactured microfluidic chip, FIG. 3[c] schematically shows a procedure of manufacturing a microfiber through reaction with calcium alginate and FIG. 3[d] is an electron microscopic image of a coaxial channel used to manufacture a microfiber.

FIG. 4 schematically shows a microfluidic chip having two sample channels. Each sample channel can be controlled by controlling a valve connected thereto and, through this, fibers of various shapes and kinds can be manufactured.

FIG. 5 schematically shows a procedure of manufacturing a cylinder channel and a coaxial channel.

FIG. 6a shows an experimental setup wherein a microvalve is connected with a PC (LabVIEW) for automatic control of the valve, FIG. 6b is a SEM image of a membrane portion of the microvalve and FIG. 6c is an image of a valve and an air channel connected to an actual chip. When air is injected into the air channel, the valve is 'closed' and sample flow is stopped. When air is discharged (vnet), the channel is 'opened' and sample flow occurs again.

FIG. 7 shows an image of a fibrous scaffold manufactured using a fiber generating chip.

FIG. 8a shows a procedure of testing whether a microfluidic chip operates properly using a dye. The images on the right side of FIG. 8a show that a sample does not flow through a channel when a valve is closed and flows only through a fiber generating portion when the valve is opened.

FIG. 8b shows fibers manufactured using a fiber generating chip having two sample channels and cut with a microvalve.

FIG. 9 shows fibers of various shapes manufactured using a microfluidic chip according to the present disclosure.

FIG. 10 shows fibers of various kinds manufactured using a microfluidic chip according to the present disclosure.

FIG. 11 and FIG. 12 show procedures of manufacturing fibers using a microfluidic chip according to the present disclosure.

FIG. 13 shows production of a fiber by a spider using a silk gland and a spigot.

FIG. 14 shows an air channel and a microvalve. The microvalve operates as pressure is applied from the air channel.

FIG. 15 shows an axial symmetry model for estimating a membrane thickness of a microvalve.

FIG. 16 shows a diagram for calculating the volume of a prepolymer PDMS.

FIG. 17 shows the relationship between volume of a prepolymer PDMS and the thickness of a PDMS membrane.

FIG. 18 shows the change of a fiber diameter depending on the air pressure applied to a valve.

FIG. 19 shows the change of the length of a cut fiber depending on the sample injection rate.

FIG. 20 shows the volume of the water drop of FIG. 9 a depending on the size of a spindle-knot.

BEST MODE

Hereinafter, various aspects and embodiments of the present disclosure will be described in detail.

In an aspect, the present disclosure provides a microvalve including a thin membrane made of a polymer below a hole 1.5-4 mm in diameter which perforates a microfluidic chip.

The hole may have a diameter of specifically 1.5-4 mm, more specifically 2-3 mm. If the hole diameter is smaller than 1.5 mm, reflection may not occur as desired in response to a pressure applied from an air channel. And, if the hole diameter is larger than 4 mm, fine-tuning is difficult because of large effect from the air channel.

Specifically, the thin membrane may be curved such that a center portion is thinner and a wall portion is thicker, with the center portion of the thin membrane being 1-30 μm in thickness (x). If the thickness is smaller than 1 μm, the membrane may not endure pressure and become damaged. And, if the thickness is larger than 30 μm, reflection may not occur as desired inside the valve in response to the pressure applied from the air channel.

The polymer is not particularly limited in its kind. For example, it may be selected from PDMS, rubber, polybutadiene, polyisobutylene, polyurethane, a combination thereof and a prepolymer thereof.

In another aspect, the present disclosure provides a method for manufacturing a microvalve by perforating a chip, injecting a polymer material and curing same, which includes: (a) making a hole perforating a microfluidic chip; (b) placing the chip on a film; (c) forming a thin membrane by injecting a liquid polymer into the hole; (d) curing the thin membrane; and (e) removing the film.

In (a), wherein the hole perforating the microfluidic chip may have a diameter of specifically 1.5-4 mm, more specifically 2-3 mm. If the hole diameter is smaller than 1.5 mm, reflection may not occur as desired in response to a pressure applied from an air channel. And, if the hole diameter is larger than 4 mm, fine-tuning is difficult because of large effect from the air channel.

In (b), the film is not particularly limited in its kind. For example, it may be PE, PP, etc.

In (c), the liquid polymer is not particularly limited in its kind. For example, it may be an elastomer selected from PDMS, rubber, polybutadiene, polyisobutylene, polyurethane, a combination thereof and a prepolymer thereof, specifically prepolymer PDMS, but is not limited thereto.

The PDMS refers to poly(dimethylsiloxane). Any PDMS can be used as long as it has a molecular weight in the range commonly used in the art to which the present disclosure belongs.

In (c), the liquid polymer may be used in an amount of specifically 1.5-4 μL, more specifically 2.5-3 μL. Outside this range, a membrane with a desired thickness cannot be obtained.

In (c), the thin membrane is formed by surface tension. Since the intrinsic property of the material is used, the manufacturing process is very easy and highly reproducible.

Specifically, the thin membrane may have a thickness of 1-30 μm at a center portion thereof. If the thickness is smaller than 1 μm, the membrane may not endure pressure and become damaged. And, if the thickness is larger than 30 μm, reflection may not occur as desired inside the valve in response to the pressure applied from the air channel.

In (d), the curing of the thin membrane may be carried out by baking the microfluidic chip in an oven at 70-90° C. for 1.5-3 hours. Outside this range, the polymer material may be easily deformable or brittle.

In another aspect, the present disclosure provides a microfluidic chip including a microvalve including the thin membrane according to the present disclosure (hereinafter, also referred to as a polymer thin membrane). The microfluidic chip includes (1) a first layer including an air channel, (2) a second layer including a microvalve and (3) a third layer including a coaxial sample channel.

One end of the air channel may serve as an air inlet and the other end may be connected to an upper end of the microvalve such that air pressure can be applied from the air channel to the microvalve.

The upper end of microvalve may be connected to the air channel and a lower end may be blocked by a polymer thin membrane. The polymer thin membrane may be positioned on the coaxial sample channel and the sample amount may be controlled by the pressure applied to the microvalve as the polymer thin membrane swells downward and presses the coaxial sample channel.

The air channel is a channel through which air can flow. Since it is connected to the microvalve, when air is injected into the air channel, pressure may be applied to the microvalve, thereby inducing reflection of the membrane of the microvalve and pressing the sample channel so as to control the amount of sample flowing in the sample channel. When air is discharged, the membrane of the microvalve returns to the original state and the sample can freely flow in the sample channel.

In an exemplary embodiment, referring to FIG. 6c, when air is injected into the air channel, the valve is 'closed' and sample flow is stopped. When air is discharged (vnet), the channel is 'opened' and sample flow occurs again.

Accordingly, when air is injected into an inlet of the air channel of the microfluidic chip according to the present disclosure, the air applies pressure to the hole of the valve in the middle layer adjacent to the air channel as it flows through the air channel in the upper layer. Owing to reflection by the pressure, the pressure at the lower portion of the membrane becomes lower than that at the upper portion thereof, and the membrane is deformed toward the lower portion due to the pressure difference. In this way, the fluid flow through the sample channel and sample amount can be controlled.

In an exemplary embodiment of the present disclosure, the coaxial channel may be a cylinder channel generating a coaxial flow and may include one or more sample channel, a main channel and one or more external channel, being formed by molded parts of semicylindrical channels bonded with each other. At least one of the one or more sample channel, the main channel and the one or more external channel may be a cylinder channel having a circular or oval cross section. A terminal end of the one or more sample channel may be connected to an initial end of the main channel. The terminal end portion of the one or more sample channel connected to the main channel may be tapered and the remaining portion may be constant in size and shape of the cross section. The one or more external channel may be connected to a side of the main channel.

In the present disclosure, the initial end and the terminal end of the channel refer to an end portion where the flow of a medium in the channel begins and an end portion where the flow of the medium ends, respectively.

The cylinder channel may have a circular or oval cross section. In the present disclosure, "circular or oval" does not necessarily mean geometrically perfect circular or oval shape but includes shapes that are close thereto. That is to say, it should be understood that not only the shapes wherein the two semicylindrical channels are connected as smooth curves (FIG. 2[a], [b]) but also the shapes wherein the semicylindrical channels are connected with sharp points (FIG. 2[c], [d]).

The channel may (i) be constant in size along a longitudinal direction, (ii) decrease or increase linearly in size along the longitudinal direction or (iii) be constant and then decrease or increase linearly in size along the longitudinal direction as a combination of (i) and (ii).

(i) The sample channel may be tapered toward the terminal end portion or (ii) only the terminal end portion of the sample channel may be tapered toward the portion connected with the main channel and the remaining portion may be constant in size and shape of the cross section.

The sample channel is a channel through which a sample (fluid) flows. The sample flowing out of the one or more sample channel enters the main channel connected to the end portion of the sample channel and is cured after meeting with a material coming out of the external channel connected to the side of the main.

Specifically, a longitudinal axis in the main channel may be in line with a longitudinal axis in the sample channel and a longitudinal axis in the external channel may cross with a longitudinal axis in the main channel. Particularly, all the longitudinal axes in the main channel, the sample channel and the external channel may be in the same plane. In this case, the effect desired by the present disclosure can be achieved effectively.

In another aspect, the present disclosure provides a method for manufacturing a microfluidic chip, including: positioning a third layer including a coaxial sample channel below a second layer including a microvalve and bonding them using oxygen plasma; and positioning a first layer on the second layer and bonding them using oxygen plasma, wherein the second layer is prepared by (a), (b), (c), (d) and (e).

The coaxial channel may be prepared by: (A) positioning a membrane on a base mold having a long groove and adjusting pressure such that the pressure at the lower portion of the membrane is lower than the pressure at the upper portion and the membrane is deformed at the lower portion on the groove due to the pressure difference; (B) positioning a photosensitive material on the deformed membrane, positioning a light-transmitting material on the photosensitive material and preparing a master mold including the photosensitive material by irradiating light onto the light-transmitting material; and (C) preparing molded parts including semicylindrical channels using the master mold and bonding the two molded parts including the semicylindrical channels.

The preparation of the semicylindrical channel using the master mold may be achieved by a method commonly employed in the art to which the present disclosure belongs.

In (A), the material of the base mold is not particularly limited. For example, PDMS, PMMA, plastic or cast metal such as gold or iron may be specifically used. More specifically, PDMS may be used.

The material of the membrane is not particularly limited. For example, an elastomer selected from PDMS, rubber, polybutadiene, polyisobutylene and polyurethane may be specifically used. More specifically, PDMS may be used.

The materials of the membrane and the base mold may be either identical or different. The thickness of the membrane may be determined adequately by those skilled in the art to achieve the effect desired by the present disclosure based on the present disclosure. Specifically, the effect desired by the present disclosure may be effectively achieved when the thickness is 10-20 μm.

The groove of the base mold may be formed by a soft lithography process, without being limited thereto. It is desired that the groove is deep enough such that the membrane touches the bottom of the groove even after being deformed by the pressure difference. The groove may have a depth of specifically a half of its width or larger, more specifically a depth of the width of the groove or larger. The bottom of the groove may be flat, but is not limited thereto.

In (B), the material of the photosensitive material may be selected from SU-8, AZ PR and Norland Optical Adhesive (NOA), although not being limited thereto. More specifically, it may be SU-8. The material of the light-transmitting material may be selected from glass, quartz, plastic, polystyrene, polyethylene, etc., although not being limited thereto. More specifically, it may be glass or quartz.

The SU-8 refers to a material having the following chemical formula. Any SU-8 can be used as long as it has a molecular weight in the range commonly used in the art to which the present disclosure belongs.

[Chemical Formula 1]

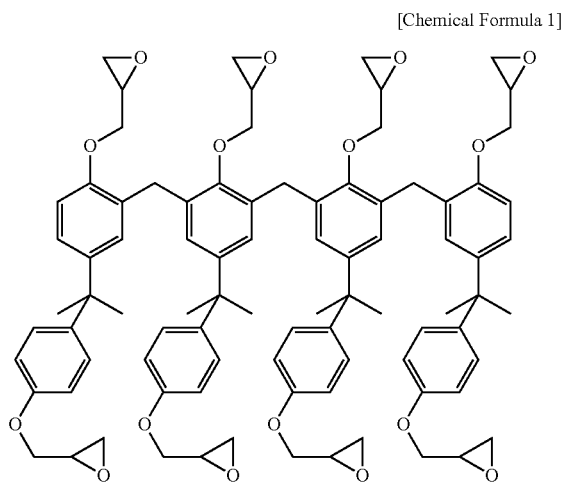 [SMILES: CC(C)(c1ccc(OCC2CO2)cc1)c1ccc(OCC2CO2)c(Cc2cc(C(C)(C)c3ccc(OCC4CO4)cc3)cc(Cc3cc(C(C)(C)c4ccc(OCC5CO5)cc4)cc(Cc4cc(C(C)(C)c5ccc(OCC6CO6)cc5)ccc4OCC4CO4)c3OCC3CO3)c2OCC2CO2)c1]

The light may be UV or visible light. Specifically, the effect desired by the present disclosure may be achieved effectively when the light is UV.

In (C), the material of the molded part including the semicylindrical channel may be selected from PDMS, NOA, PMMA and acryl. But, without being limited thereto, any material can be used as long as it has a molecular weight in the range commonly used in the art to which the present disclosure belongs. The PDMS refers to poly(dimethylsiloxane).

The groove of the base mold may be formed by a soft lithography process, although not being limited thereto. And, the bonding of the two molded parts including the semicylindrical channels may be carried out using oxygen plasma, although not being limited thereto.

In another aspect, the present disclosure provides a method for manufacturing a microfiber using the microfluidic chip according to the present disclosure, including: (A) injecting a sample material into the sample channel; (B) injecting an external material into the external channel; and (C) controlling the microvalve.

In an exemplary embodiment, (A) and (B) may be carried out simultaneously. Alternatively, they may be carried out sequentially, continuously or intermittently with time interval. (C) is carried out following (A) and (B) for control of fluid flow and sample amount.

In another exemplary embodiment, the sample material may be (i) a non-UV-curable material such as PLGA, alginate, chitosan, collagen, etc., (ii) a UV-curable material such as 4-HBA, PNIPAAM, NOA, PEG, etc. or (iii) a mixture thereof, although not being limited thereto.

In another exemplary embodiment, the external material may be a solution wherein (i) a first external material selected from calcium chloride, sodium chloride and a mixture thereof is dissolved in (ii) a second external material selected from water, cell culture, PBS and a mixture thereof. In this case, the effect desired by the present disclosure can be achieved effectively.

In another aspect, the present disclosure provides a method for controlling the diameter of a microfiber of a sample material manufactured using the microfluidic chip according to the present disclosure, including controlling (i) the pressure of air injected into the microvalve, (ii) the injection speed of a sample material into the sample channel and (iii) the injection speed of an external material into the external channel.

In an exemplary embodiment, (i) the pressure of the air injected into the microvalve may be controlled in the range of specifically 0-300 kPa, although not particularly limited thereto, (ii) the injection speed of the sample material into the sample channel may be controlled in the range of specifically 3-30 μL/min, more specifically 5-20 μL/min, and (iii) the injection speed of the external material into the external channel may be controlled in the range of specifically 10-50 mL/h, more specifically 20-30 mL/h. In this case, the effect desired by the present disclosure can be achieved effectively.

In another aspect, the present disclosure provides a method for manufacturing a microparticle using the microfluidic chip according to the present disclosure, including: (A) injecting a sample material into the sample channel; (B) injecting an external material into the external channel; and (C) controlling the microvalve.

In an exemplary embodiment, (A) and (B) may be carried out simultaneously. Alternatively, they may be carried out sequentially, continuously or intermittently with time interval. (C) is carried out following (A) and (B) for control of fluid flow and sample amount.

In another exemplary embodiment, the sample material may be (i) a non-UV-curable material such as PLGA, alginate, chitosan, collagen, etc., (ii) a UV-curable material such as 4-HBA, PNIPAAM, NOA, PEG, etc. or (iii) a mixture thereof, although not being limited thereto.

In another exemplary embodiment, the external material may be a solution wherein (i) a first external material selected from calcium chloride, sodium chloride, etc. is dissolved in (ii) a second external material selected from organic solvents such as oleic acid, soybean oil, methanol, dodecane, etc.

In particular, when the external material is prepared by: (a) preparing a first external material solution by dissolving the first external material in a third external material selected from 2-methyl-1-propanol, isopropyl alcohol and a mixture thereof; (b) preparing a mixture solution by mixing the first external material solution with the third external material; and (c) distilling the mixture solution, the effect desired by the present disclosure can be achieved effectively.

In another aspect, the present disclosure provides a method for controlling the diameter of a microparticle manufactured using the microfluidic chip according to the present disclosure, including controlling (i) the pressure of air injected into the microvalve, (ii) the injection speed of a sample material into the sample channel and (iii) the injection speed of an external material into the external channel.

In an exemplary embodiment, (i) the pressure of the air injected into the microvalve may be controlled in the range of specifically 0-300 kPa, although not particularly limited thereto, (ii) the injection speed of the sample material into the sample channel may be controlled in the range of specifically 3-30 μL/min, more specifically 5-20 μL/min, and (iii) the injection speed of the external material into the external channel may be controlled in the range of specifically 10-50 mL/h, more specifically 20-30 mL/h. In this case, the effect desired by the present disclosure can be achieved effectively.

MODE FOR INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLES

<Manufacturing of Microfluidic Chip>
Manufacturing of Microvalve

Referring to FIG. 1, a hole with a diameter of 3 mm perforating a microfluidic chip was made and an OHP film was placed thereon. Then, 2 μL of prepolymer PDMS was injected. Owing to surface tension, a thin layer was formed below the hole. Subsequently, the PDMS in the hole was cured by baking in an oven at 80° C. for 2 hours. A microvalve was obtained after removing the OHP film.

Manufacturing of PDMS Air Channel

A PDMS mold was manufactured first by a soft lithography process and then an SU-8 master mold was formed through deformation and replication of membrane. A semicylindrical PDMS channel was manufactured through replication of the SU-8 mold. Two semicylindrical PDMS channels were bonded using oxygen plasma to manufacture an air channel (see FIG. 5).

Manufacturing of PDMS Coaxial Channel

A PDMS-based cylinder channel was manufactured through replication of PDMS membrane, as shown in FIG. 5.

First, a PDMS-based mold was manufactured by a soft lithography process and a PDMS membrane was placed on the mold. Then, a concave semicylindrical channel structure was formed by depressurizing the lower portion. After pouring SU-8 and curing by irradiating UV, a semicylindrically deformed membrane was prepared and also a concave semicylindrical SU-8 master mold was formed. In this manner, semicylindrical structures of various shapes and dimensions such as pseudo-rectangular structure, combined structure, tapered structure and coaxial structure shown in FIG. 5[b] were manufactured.

For example, the combined structure was formed using base molds having different depths. The shallow portion has a pseudo-rectangular shape as the deformed membrane spreads out at the bottom of the channel, whereas the membrane is deformed to form a cylindrical structure at the deep portion.

A method for manufacturing a coaxial channel is shown in FIG. 5[c]. A PDMS base mold was prepared first and then an SU-8 master mold was formed through deformation and replication of membrane. A semicylindrical PDMS channel was prepared through replication of the SU-8 mold and two concave semicylindrical PDMS channels were bonded using oxygen plasma to manufacture the coaxial channel.

In the same manner, a coaxial channel having two sample channels (FIG. 4), a coaxial channel having three sample channels (not shown) and a coaxial channel having six sample channels (FIG. 3[b]) were prepared.

Manufacturing of Microfluidic Chip

Referring to FIG. 3[b], the microvalve prepared above was bonded with the coaxial sample channel using oxygen plasma. Then, the air channel prepared above was placed on the microvalve and bonded using oxygen plasma to prepare a microfluidic chip including the air channel, the microvalve and the coaxial channel.

<Membrane Thickness of Microvalve>

When air is injected into the air channel of the prepared microfluidic chip, air pressure is applied to the microvalve and the sample channel is blocked due to reflection. FIG. 1b shows a result of simulation along the cross section of the valve using a 2D axial symmetry model to estimate membrane thickness at the center of the hole, which can be calculated from the radius of the hole and the contact angle between air, the prepolymer PDMS and the PDMS. The method is illustrated in FIG. 15 and described below.

The volume of PDMS in FIG. 17 was calculated as follows.

The surface of the prepolymer PDMS inside the hole is a part of a sphere having a radius adequate to exhibit the curvature shown in FIG. 15. The relevant analytical equation is based on the principle that the volume of the shaded portion ($V_{pre}$) is identical to the initial volume (a) of the prepolymer PDMS before physical contact.

Referring to FIG. 16, the volume of the shaded portion of the prepolymer PDMS can be calculated by subtracting the volume of the spherical portion ($V_{seg}$) from the volume of the cylinder ($V_{cyl}$).

$$a = V_{pre} = V_{cyl} - V_{seg} \tag{1}$$

The volume of the spherical portion and the volume of the cylinder may be expressed by the following equations:

$$V_{seg} = \frac{\pi R^3}{3}(2 - 2\sin\theta - \cos^2\theta \sin\theta), \tag{2}$$

$$V_{cyl} = \left(\frac{s}{2}\right)^2 \pi \cdot h \tag{3}$$

wherein θ is the contact angle of the prepolymer PDMS against the surface of PDMS and s is the hole diameter, R is the radius of curvature of the PDMS surface (inner valve) and h is the maximum height of the PDMS valve.

The radius R and the height h may be expressed by the following equations:

$$R = \frac{s}{2\cos\theta}, \quad (4)$$

$$h = x + \frac{s}{2}(\sec\theta - \tan\theta) \quad (5)$$

wherein x is the minimum thickness (thickness of the center portion) of the PDMS valve.

Accordingly, the initial volume (a) may be expressed with the minimum thickness (x), contact angle (θ) and hole diameter (s) as follows from the equations (1), (2), (3), (4) and (5).

$$a = \frac{\pi s^2}{24}(6x + 3s\sec\theta - 2s\sec^3\theta + 2s\tan^3\theta) \quad (6)$$

Finally, the minimum thickness of the PDMS valve, x, may be defined as follows.

$$x = \frac{1}{6}\left(\frac{24}{\pi s^2} - 3s\sec\theta + 2s\sec^3\theta - 2s\tan^3\theta\right) \quad (7)$$

The contact angle θ of liquid PDMS measured on the wall of the PDMS was ~15° and the hole diameter s is a constant. Therefore, the thickness of the membrane is determined by the volume of the PDMS prepolymer only. The simulation result of the minimum thickness of PDMS in the valve was analyzed by computational fluid dynamics (COMSOL, MA) using the 2D axial symmetry model. The surface tension at the boundary between the liquid PDMS and air was set as 0.19 N/m.

<Operation of Microvalve>

A method of operating a valve in a channel through which a fluid flows is shown in FIG. 6. First, an on/off signal is input from a LabVIEW PC board to a solenoid valve. This signal controls a switch of the solenoid valve and the time during which air compressed by a compressor enters a fiber generating channel can be controlled thereby. The on/off signal was programmed to be controllable with 1/100-second frequency and delay was used to utilize more signals. Each channel was connected to the microvalve and the solenoid valve and they were controlled by one PC. FIG. 6b shows electron microscopic images of the membrane used in the experiment. An air pressure of about 200 kPa was used to operate a 20-μm thick membrane. FIG. 6c shows that the sample channel is blocked as air is injected and discharged.

Manufacturing of Fiber Generating Chip

As an example of the microfluidic chip, a fiber generating chip capable of producing microfibers of various shapes and functions was manufactured. The actual spider produces silk from spigots while controlling sample amount through the silk gland.

As seen from FIG. 13, the silk gland and the spigot of the spider may be mimicked with the coaxial channel and the valve. As the real spider does, a fiber can be cut using the valve and a fiber consisting of different samples can be produced using different sample channels connected with each other.

In order to realize such function, as shown in FIG. 3[a], the fiber generating chip has a portion that controls fluid amount using a thin sample injecting channel and a microvalve (artificial gland) and a portion that produces a microfiber from different samples (artificial spigot). Each channel is connected with each valve to allow control of fluid flow. A microfluidic chip manufactured using PDMS is shown in FIG. 3[b]. The channel shown in FIG. 3[b] consists of three layers—a first layer (upper layer), a second layer (middle layer) and a third layer (lower layer). The first layer, through which air can come in and out, is connected to a valve hole of the second layer. The valve hole is connected to a sample channel of the lower layer but is separated by a thin membrane. After entering the upper channel, a fluid flows into the cylindrical channel toward the exit and a microfiber is produced through reaction with calcium alginate, as shown in FIG. 3[c]. FIG. 3[d] is an electron microscopic image of a coaxial channel used to manufacture the microfiber.

Fiber Production Through Control of Air Pressure and Sample Material Injection Rate FIG. 7 shows an image of a fibrous scaffold manufactured using the fiber generating chip. When manufacturing the scaffold, the fiber thickness was controlled using the valve. The insert image shows that the fiber thickness can be controlled by controlling the valve pressure. The valve connected to the sample channel was operated by controlling pressure and only one sample channel was used to produce a fiber. Referring to FIG. 7, the fiber thickness was observed while varying the air pressure applied to the microvalve at 200 kPa, 100 kPa and 0 kPa. It can be seen that the fiber is the thinnest when the pressure was 200 kPa and is the thickest when no pressure was applied.

FIG. 18 shows the change of the fiber diameter depending on the air pressure applied to a valve. It can be seen that, given the same air pressure, the fiber thickness varies with the sample pressure (fluid pressure).

Manufacturing of Fiber Using Microfluidic Chip

FIG. 4 schematically shows a microfluidic chip having two sample channels. Each sample channel can be controlled by controlling a valve connected thereto and, through this, fibers of various shapes and kinds were manufactured. FIG. 8a shows a fiber generating chip having six sample channels.

As seen from FIG. 8, it was tested whether the chip operates properly using a dye. The images on the right side of FIG. 8a show that the sample does not flow through a channel when a valve is closed and flows only through a fiber generating portion when the valve is opened.

FIG. 8b shows fibers manufactured using the fiber generating chip having two sample channels and cut with the valve.

Alginate sample was injected into a sample channel on one side and PBS was injected into a sample channel on the other side. Then, the valve on/off signal was controlled as follows. An on signal was supplied to the sample channel to which the PBS was injected and a controlled valve on/off signal was supplied to the sample channel to which the alginate was injected. As a result, fibers of different lengths were prepared depending on the valve opening time as shown in the right-side images of FIG. 8b.

1% alginate powder/water was used as the sample material. The sample was injected at a rate of approximately 5-20 μL/min. As a solvent for solidifying the alginate, 1% CaCl$_2$/ water was injected at a rate of approximately 20-30 mL/h. The result is shown in FIG. 19.

As a result, bot the thickness and the length could be controlled by controlling the injection rate of the alginate sample and the valve opening time. Accordingly, it can be seen that the fiber diameter can be controlled with the sample injection rate.

FIG. 9 shows fibers of various shapes manufactured using the fiber generating chip having two sample channels equipped with the valves (The method for manufacturing the fibers is described in FIG. 11.).

FIG. 9a shows an alginate fiber having artificial spindle-knots and joints likes those of real spider silk. The artificial spindle-knots were formed from swollen pores of alginate gel by mixing alginate with salt. It can be seen that a water drops dropped on the fiber move toward the artificial spindle-knot having large surface area, as in the real spider silk. FIG. 9b is an electron microscopic image of the spindle-knot. Large holes are observed in the alginate gel.

FIG. 20 shows the volume of the water drop of FIG. 9a depending on the size of the spindle-knot. It can be seen that the size of water drop changes linearly with the length of the spindle-knot in axial direction. FIG. 9d shows air bubbles trapped in the fiber. The method for manufacturing same is described in FIG. 11a.

The SEM image of FIG. 9d was obtained while injecting air compressed at 10 kPa into the channel on one side. The trapped air was not discharged even after time until the fiber was taken out of the solution. The fiber diameter was controlled by the sample injection rate of approximately 5-20 µL/min. The sample material was 1% alginate powder/water and 1% $CaCl_2$/water was used as a solvent for solidifying alginate. The injection rate of $CaCl_2$ was approximately 20-30 mL/h.

FIG. 10 shows fibers of various kinds manufactured using a fiber generating chip having three sample channels. The fluorescence images show that three different samples having various patterns are coded in one fiber. The method for manufacturing the fiber using the three samples is described in FIG. 12. The sample material was 1% alginate powder/water mixed with 300-nm PS fluorescent beads at 0.05% and 1% $CaCl_2$/water was used as a solvent for solidifying alginate. The sample injection rate was 5-20 µL/min and the $CaCl_2$ injection rate was approximately 20-30 mL/h.

FIG. 10a is a fluorescence microscopic image showing that the fiber was parallel-coded axially without using a valve. FIG. 10b shows a fluorescence image coded with regular intervals by operating three valves continuously. FIG. 10c is similar to FIG. 10b, except that spindle-knots were formed through overlapping. FIG. 10d is a combination of FIG. 10a and FIG. 10b.

The fibers with various shapes and coding methods thereof are shown in FIGS. 10 and 11. Details are as follows.

A spinning chip having two channels was used to produce fibers of various shapes. Two sample fluids were injected into the channels, respectively. The "on-off" of each channel was controlled by an electrical signal.

Details are as follows.

1) Bubble-Embedded Fiber

Air was injected into an air channel with a pressure of 10-50 kPa. 2 wt % alginate solution containing 1% surfactant was injected into a sample channel. The surfactant was used to prevent solidification of air bubbles. Subsequently, uniformly dispersed bubbles were introduced into a fiber. The flow rate of the alginate solution and the $CaCl_2$ solution was 20-50 µL/min and 20-40 mL/h, respectively.

2) Cut Fiber

PBS and alginate solution were randomly injected into respective sample channels. Each valve was opened randomly to prepare cut fibers with regular lengths. The length of the fiber was controlled by varying the opening time of each valve. To obtain a longer fiber, a longer opening time is required for the alginate channel.

3) Embossed Fiber

The same alginate solution was injected into each sample channel, but with different flow rate for each channel. The valve opening time was randomly changed to obtain fibers of varying diameters.

4) Tapered Fiber

The same alginate solution was injected into each channel, but the valve "on/off" was varied. For example, the sequence for sample 1 was "on" for 0.4 second and "off" for 0.2 second, periodically. Conversely, the sequence for sample 2 was "on" for 0.2 second and "off" for 0.4 second, with 0.2-second delay. The total volume was changed gradually to produce a tapered fiber. A small fiber diameter was obtained when both the channels were closed.

Manufacturing of Fiber by Spatiotemporal Encoding

FIG. 12 shows a method for preparing encoded fibers with different compositions. Three channels were used and fibers including a diver coding scheme were produced by controlling 'on-off' sequences. For serial coding, the three sample channels were opened sequentially and the minimum opening time ('open' signal) was 3 seconds. In the same manner, an embossed and serially coded fiber was prepared by injecting the sample with delay. However, the 'open' signal was overlapped within ~0.1 second. Also, a fiber was prepared by combining serial and parallel coding. The same signal was used as in serial coding and open signal was added for all the samples. For better visualization, fluorescent microspheres were prepared from red, green and blue polystyrene (300-nm sized PS beads, Thermo) and mixed with 0.05% alginate solution.

The present disclosure provides a microvalve which is not completely separated from a channel and a method for manufacturing a microvalve by making a hole perforating a microfluidic chip, forming a thin membrane by injecting a liquid polymer into the hole and then baking same. A microvalve can be manufactured by making a 2-3 mm hole perforating a microfluidic chip, forming a thin membrane by injecting a liquid polymer into the hole and then baking the thin membrane. Fibers of various shapes can be prepared by operating the valve.

In accordance with the present disclosure, the valve membrane can be formed simply using surface tension and the valve may be bonded with a coaxial channel to manufacture a microchip which is capable of producing microfibers of various shapes.

Since the coaxial channel is used, microfibers can be prepared continuously without blocking. In general, even a quadrangular particle generating channel requires surface treatment for lubrication and continuous production of fiber is very difficult. The use of the PDMS coaxial channel allows very easy preparation of particles and fibers. The produced particles and fibers were uniform with deviation within ±3%. Accordingly, it can be seen that the method of the present disclosure is remarkably improved in producing particles and fibers of various shapes.

The present disclosure also provides a combined channel in which a square or quadrangular channel is combined with a coaxial channel. The combined channel is applicable to various fields including biomedicine and chemistry. In particular, a microfluidic platform combined with the microfluidic chip according to the present disclosure can produce various fibers and particles including various cells and biochemical molecules.

Whereas only UV-curable materials can be used in the existing system, the system of the present disclosure allows use of not only the UV-curable materials but also non-UV-curable scaffold materials such as PLGA, alginate, chitosan, etc.

The present disclosure provides a PDMS microfluid chip that can be simply and cost-effectively manufactured by preparing a membrane microvalve from a polymer material and disposing a sample channel below the valve and a novel method for producing microfibers and microparticles of various shapes using same.

INDUSTRIAL APPLICABILITY

The present disclosure provides a combined channel wherein a square or quadrangular channel is combined with a coaxial channel. The combined channel may be used to produce fibers and microstructures using the existing microfluidic technique, which may be widely applied in the fields of biomedicine or tissue engineering.

The invention claimed is:

1. A microfluidic chip comprising (1) a first layer comprising an air channel, (2) a second layer comprising a microvalve and (3) a third layer comprising a coaxial sample channel, wherein one end of the air channel serves as an air inlet and the other end is connected to an upper end of the microvalve such that air pressure can be applied from the air channel to the microvalve, the upper end of microvalve is connected to the air channel and a lower end is blocked by a polymer thin membrane, the polymer thin membrane is positioned on the coaxial sample channel and the sample amount is controlled by the pressure applied to the microvalve as the polymer thin membrane swells downward and presses the coaxial sample channel, wherein the coaxial channel is a cylinder channel generating a coaxial flow and comprises one or more sample channel, a main channel and one or more external channel, at least one of the one or more sample channel, the main channel and the one or more external channel is a cylinder channel having a circular or oval cross section, a terminal end of the one or more sample channel is connected to an initial end of the main channel, the terminal end portion of the one or more sample channel connected to the main channel is tapered and the remaining portion is constant in size and shape of the cross section and the one or more external channel is connected to a side of the main channel.

2. The microfluidic chip according to claim 1, wherein the width of the coaxial channel (i) is constant in size along a longitudinal direction, (ii) decreases or increases linearly in size along the longitudinal direction or (iii) is constant and then decreases or increases linearly in size along the longitudinal direction as a combination of (i) and (ii).

3. The microfluidic chip according to claim 1, wherein (i) the sample channel is tapered toward the terminal end portion or (ii) only the terminal end portion of the sample channel is tapered toward the portion connected with the main channel and the remaining portion is constant in size and shape of the cross section.

4. The microfluidic chip according to claim 1, wherein a longitudinal axis in the main channel is in line with a longitudinal axis in the sample channel, a longitudinal axis in the external channel crosses with a longitudinal axis in the main channel and, particularly, all the longitudinal axes in the main channel, the sample channel and the external channel are in the same plane.

* * * * *